United States Patent [19]

Cloninger

[11] 4,268,500

[45] May 19, 1981

[54] METHOD FOR TREATING HAIR TO PREVENT DRYNESS

[76] Inventor: Grace Cloninger, 15932 Georgia Ave., Paramount, Calif. 90723

[21] Appl. No.: 122,367

[22] Filed: Feb. 19, 1980

[51] Int. Cl.³ .............................................. A61K 7/06
[52] U.S. Cl. ...................................................... 424/70
[58] Field of Search .......................................... 424/70

[56] References Cited

U.S. PATENT DOCUMENTS 1,039,064   9/1912   Lynch ................................. 424/70

OTHER PUBLICATIONS

Rohrer's, Scientific Modern Beauty Culture, pp. 13, 14 & 18, (1924).
Traven, The Complete Book of Natural Cosmetics, 12/1974, pp. 43–46, 85, 142 & 152.
Pharmaceutical Formulas, 1947, vol. II, p. 884.

*Primary Examiner*—Dale R. Ore
*Attorney, Agent, or Firm*—Edgar W. Averill, Jr.

[57] ABSTRACT

A method for treating the scalp and hair utilizing the natural product known as yogurt. The method involves the steps of rubbing yogurt into the hair and onto the scalp followed by the step of covering the treated hair and scalp with an airtight cap. After a period of time, the cap is removed and the treated hair and scalp are rinsed.

3 Claims, No Drawings

METHOD FOR TREATING HAIR TO PREVENT DRYNESS

BACKGROUND OF THE DISCLOSURE

The field of the invention is hair treatment preparations and methods, and the invention relates more specifically to methods for combating dry scalp and for treating heat or sundamaged hair. People spend large amounts of time in an effort to have attractive and lusterous hair. Unfortunately, many hair colorants and bleaches are harsh on both the scalp and hair. Most permanent dyes act by permitting a colorless dye precursor to penetrate the hair followed by a step of oxidizing the precursor to a colored molecule which is held in the hair. The oxidizing agent is typically hydrogen peroxide which, of course, is a strong oxidizing agent. This oxidizing agent can be damaging both to the hair and scalp. Furthermore, many hair waving techniques utilize heat either by itself or with chemicals which also can damage the hair and scalp.

Various hairdressings and scalp treatments have been used to combat dry scalp and damaged hair. A hot oil treatment is quite popular for this purpose, but unfortunately is relatively expensive when professionally done and is of limited effectiveness. There is thus a need for an inexpensive and effective method for treating the hair and scalp which method can be carried out without the need of a professional beautician.

SUMMARY OF THE INVENTION

The present invention is for a method for treating the scalp and hair comprising rubbing yogurt onto the scalp and hair followed by covering the treated scalp and hair with an airtight cap. The cap is maintained over the hair and scalp for a period of at least five minutes and preferably for a period of about thirty minutes after which it is removed and the hair and scalp are rinsed.

DESCRIPTION OF THE PREFERRED EMBODIMENTS

Yogurt is semi-fluid fermented milk food having a smooth texture and midly sour flavor. Typically, yogurt is made by adding milk solids to cows milk and inoculating the concentrated sterilized milk with streptococcus thermophilus, lactobacillus bulgaricus or L. acidophilus. The inoculated milk is typically incubated four or five hours at about 43° to 44° celsius until a curd forms. Commercial yogurt typically contains about 5.2% lactose, 3.4% protein, 1.7% flat, 120 ml per 100 grams of calcium together with trace amounts of numerous vitamins and other substances.

In the practice of the present invention, a quantity of unflavored yogurt such as one half cup is rubbed into the hair and scalp and then the hair and scalp are covered by a plastic cap which should be relatively airtight. This should be maintained about the hair and scalp for at least five minutes and preferably for at least fifteen minutes with thirty minutes being ideal. It has been observed that the yogurt, hair and scalp when so surrounded creates its own heat which it is believed helps the absorbtion of a portion of the yogurt into the hair and scalp. After about thirty minutes, the cap is removed and the remaining yogurt is rinsed out with cool water. The hair can then be shampooed with conventional shampoo but the treated hair will have a higher shine and the treated scalp will have lost its dryness. It is unnecessary to use a cream rinse following shampooing.

The resulting benefits of the treatment not only include the above-mentioned shininess and silkiness of the hair and reduce dryness of the scalp, but also because of the relatively low cost of yogurt, the treatment may be carried out very economically with a mild natural product. It is not known which of the ingredients of the yogurt brings about the beneficial results noted however, the yogurt, in addition to the above-mentioned ingredients, also contains many vitamins and trace minerals which may be beneficial. A definite benefit arises from the use of the airtight cap and it is believed that the warmth created assists in the treatment of the scalp and hair.

The present embodiments of this invention are thus to be considered in all respects as illustrative and not restrictive, the scope of the invention be indicated by the appended claims rather than by the foregoing description. All changes which come within the meaning and range of equivalency of the claims therefore are intended to be embraced therein.

What is claimed is:

1. A method for treating the scalp to combat dryness and produce lustrous hair comprising:
   rubbing about one-half cup of yogurt onto to the scalp and hair;
   covering the treated scalp and hair with an airtight cap;
   maintaining the hair in a covered condition for at least five minutes;
   removing the cap; and
   rinsing the scalp and hair to remove the residual yogurt.

2. The method of claim 1 wherein the cap is maintained over the treated scalp and hair for at least ten minutes.

3. The method of claim 1 wherein the cap is maintained about the treated hair and scalp for about thirty minutes.